United States Patent [19]
Pantini

[11] Patent Number: 6,080,795
[45] Date of Patent: Jun. 27, 2000

[54] PROTECTIVE FOAMS BASED ON PERFLUOROPOLYETHERS

[75] Inventor: Giovanni Pantini, Milan, Italy

[73] Assignee: Ausimont S.p.A., Milan, Italy

[21] Appl. No.: 09/037,060

[22] Filed: Mar. 9, 1998

[30] Foreign Application Priority Data

Mar. 11, 1997 [IT] Italy ................................. MI97A0523

[51] Int. Cl.⁷ ...................................................... C08J 9/00
[52] U.S. Cl. ............................................................ 521/50
[58] Field of Search ................................................ 521/50

[56] References Cited

U.S. PATENT DOCUMENTS

| | | | |
|---|---|---|---|
| 3,242,218 | 3/1966 | Miller | 528/170 |
| 3,665,041 | 5/1972 | Sianesi et al. | 528/170 |
| 3,715,378 | 2/1973 | Sianesi et al. | 528/170 |
| 4,523,039 | 6/1985 | Lagow et al. | 568/615 |
| 5,144,092 | 9/1992 | Marraccini et al. | 568/615 |

FOREIGN PATENT DOCUMENTS

| | | |
|---|---|---|
| 0 148 482 | 7/1985 | European Pat. Off. |
| 0 194 097 | 9/1986 | European Pat. Off. |
| 0 360 292 A2 | 3/1990 | European Pat. Off. |
| 1104482 | 2/1968 | United Kingdom. |

OTHER PUBLICATIONS

P.J. Frosch et al, "Efficacy of Skin Barrier Creams", Contact Dermatitis, 1993, 29, pp. 74–77.

Section Ch, Week 8728; Derwent Publications Ltd., London, GB; Class A96, AN 87–193873; SP002067699 & JP 62 016 411 A.

*Primary Examiner*—Terressa M. Boykin
*Attorney, Agent, or Firm*—Arent Fox Kintner Plotkin Kahn

[57] ABSTRACT

Foams based on the following components:
- a) a fluid emulsion comprising:
  - a perfluoropolyether, as main protective agent,
  - polar and non polar oils,
  - an acrylic copolymer characterized by hydrophilic and hydrophobic groups, and activity of primary emulsifier after neutralization with alkales,
  - an ionic surfactant (as foaming agent) water
- b) a propellant.

33 Claims, No Drawings

PROTECTIVE FOAMS BASED ON PERFLUOROPOLYETHERS

The present invention relates to compositions to be used under foam form, capable of developing a protective action towards irritating agents (acids, bases, solvents, detergents) and allergens.

The use of protective foams, in particular for hand protection, is well known in the art. It has been continuously re-proposed on the market since several years the presentation of products preferred to the "invisible glove"or "liquid glove" concept. These products fell within the most general category of the so called "barrier" products since they should be capable of assuring a perfect protection against the aggresive agents by a protective "shield" as impenetrable. Notwithstanding the barrier products were and are the answer to a real need of the market, their success has always been limited especially owing to their insufficient protective effectiveness and owing to their unsatisfactory cosmetic properties from the agreeableness point of view, since they generally result sticky and greasy.

In particular the market has generally remained disappointed by the barrier products of the protective foam type, which have occasionally had temporary successes in consequence of the commercial launching of a new product. From the application point of view, the protective foams are placed near the other barrier products (creams, lotions and pastes), however they show the advantage of a more hygienic and more practical use since a more uniform application is possible. These are appreciable aspects, especially in the case of professional use, for the prevention of hand irritating dermatitis. They are pathologies of difficult treatment once chronicized, and bound to professional and domestic activities (in the research laboratories, in industry, in the machine shops; in the medical-hospital field, in building, etc.).

From the formulation point of view, the protective foams are preparations obtained by a technique developed for other purposes. One usually applies indeed to the incorporation of emollients (mineral oils, silicones, etc.) and wetting agents (glycerine, propylenic glycol, etc.) in a base which is essentially a shaving foam, where the foaming action is obtained by the combined effect of a propellant (usually a liquefied hydrocarbon gas) with a foaming agent formed by stearic acid partially or totally neutralized with potash or with an amine. In this way the same stearic acid, optionally in excess, would develop a protective action which is added to that of the other emollients, present however at a few percent units level in order not to worse the foam quality. The known foams described above show a good stability of the composition inside the bombs, essential feature not to have segregation of the composition components (obviously the propellant component is not considered). However they have the drawback not to be able of leading to the formation of the so called "liquid glove". This means that the protective effectiveness is very limited and not homogeneous above all.

In the prior art there are various scientific publications wherein various inquires carried out on men are described which agree on the poor effectiveness of this kind of preparation, among which Marly Skin$^R$ is the most known (distributed by Gebro Pharma in Germany and by Trimex Trading in Switzerland) which therefore has been taken as reference product, in studies in which it was assimilated to the barrier creams category. These studies show that the foams on the market can worse the defense capacity which is typical of the skin towards irritating agents such as acids, alkales, surfactants and organic solvents. This is explained by the fact that the presence of soaps (for instance stearic acid neutralized by alkales) would develop even a vehicle function for the aggressive agents, of irritative or also allergic type. See for instance "Efficacy of skin barrier creams (II)" P. J. Frosch et al., Contact Dermatitis, 1993, 29, 74–77.

It is also known that the introduction of perfluoropolyethers, compounds having hydrophobic and lipophobic characteristics, has allowed the carrying out of potentially multifunctional barrier creams, with high persistence however without contra-indications from the dermatological and cosmetic point of view (toxicological safety and preparations agreeableness). Some researches on men have shown the efficacy of conventional creams in which a perfluoropolyether was incorporated in the treatment of chronic hand dermatitis.

However tests carried out by the Applicant have shown that the incorporation of perfluoropolyethers in the foams described above, i.e. based on stearic acid/stearates, has not lead to foams of sufficient efficacy as regards the homogeneity of the "liquid glove" formation.

The need was felt to have available a foam having the necessary stability and homogeneity characteristics and not showing therefore the drawbacks of the known foams.

The Applicant has surprisingly and unexpectedly found compositions based on a particular emulsion to be utilized to obtain a stable and homogeneous foam thereof (with the use of a propellant) by using as foaming agents ionic surfactants.

It is an object of the present invention, therefore, a foam based on the following components:
a) a fluid emulsion comprising:
   a perfluoropolyether, as main protective agent,
   polar and non polar oils,
   an acrylic copolymer characterized by hydrophilic and hydrophobic groups, and activity of primary emulsifier after neutralization with alkales,
   water
   an ionic surfactant (as foaming agent)
b) a propellant.

The foam is characterized in being based on an emulsion which maintains stable notwithstanding the addition of foaming agent, without however the homogeneity effect in the resulting foam, due to this addition, further to the contact with the skin, fails.

The foams of the present invention are unexpectedly stable as a consequence of t he addition of the ionic foaming agent (preferably anionic, but also cationic and amphoteric), while the addition of a non ionic foaming agent unexpectedly leads to the segregation.

The bombs wherein the foams of the present invention are contained comprise as foaming agent an ionic surfactant preferably in aqueous solution with a titre between 30 and 50% by weight or dispersed/dissolved in water at 30% by weight if solid.

The concentration of the foaming agent, referred to 100 parts by weight of emulsion, is comprised between 0.1 and 5 parts, preferably between 0.3 and 3 parts, and still more preferably between 0.5 and 1.5 parts.

The stability test of the foams of the present invention was carried out as follows:
after the addition of the foaming agent to the emulsion, the stability has been verified by treatment at 40° C. for two months or by centrifugation at 4000 rpm for 10 minutes.

In all cases with the foams of the invention no segregation took place.

Moreover the compositions of the invention must meet also the stability test under pressure which is the following: addition of propellant, in amounts of 30 volumes of liquefied isobutane for 120 volumes of emulsion and it is left in bomb for three months. Then the propellant is removed.

Successively the stability tests are carried out: centrifugation at 4000 rpm for 10 minutes, or by treatment at 40° C. for 2 months. No segregation of the various phases must occur so that the test is positive.

The homogeneity test, condition necessary to obtain a liquid glove, was carried out as follows: on a format A4 photocopy paper sheet an amount from 0.5 to 1 g of foam delivered by the bomb is applied and the possible release on the paper of the emollients and the liquid protective agents with consequent formation of a wide homogeneous stain and absence of solid residue, is observed.

The emulsion to obtain foams contains the components indicated in the following amounts (parts by weight):

- a perfluoropolyether in amounts from 0.05 to 30 parts, preferably from 0.5 parts up to 5 parts (by weight). The average number molecular weight is comprised between 500 and 10000, but preferaly between 3000 and 7000,
- polar and non polar oils from 5 to 40 parts, preferably between 10 and 20,
- an acrylic copolymer characterized by hydrophilic and hydrophobic groups, and activity, after neutralization with bases, of primary emulsifier, in amount comprised in the range of 0.1–0.5 parts by weight,
- an ionic surfactant (as foaming agent) in amount comprised between 0.1 and 5 parts by weight,
- water as complement to 100 parts by weight.

The propellant amount is preferably between 20 and 40 parts by volume for 120 parts by volume of emulsion.

The perfluoropolyethers (PFPE) utilized for the preparation of the emulsion are chemically inert products, are not toxic, do not damage the ozone layer and are not flammable.

The (per)fluoropolyethers comprise repeating units statistically distributed along the polymer chain, selected from: $(CF_2CF_2O)$, $(CFYO)$ wherein Y is equal to F or $CF_3$, $(C_3F_6O)$, $(CF_2(CF_2)_zO)$ wherein z is an integer equal to 2 or 3, $(CF_2CF(OR_f)O)$, $(CF(OR_f)O)$ wherein $R_f$ is equal to —$CF_3$, —$C_2F_5$, —$C_3F_7$; —$CR_4R_5CF_2CF_2O$ wherein $R_4$ and $R_5$ are equal to or different from each other and selected from Cl or perfluoroalkyl, for instance from 1 to 4 C atoms.

The perfluoropolyethers end groups are selected from —$CF_3$, —$C_2F_5$, —$C_3F_7$, $ClCF_2CF(CF_3)$—, $CF_3CFClCF_2$—, $ClCF_2CF_2$—, $ClCF_2$—. In particular the following (per)fluoropolyethers can be mentioned as preferred which have the following repeating units:

 (a)

wherein Y is F or $CF_3$; a and b are integers such that the molecualr weight is in the range indicated; a/b is comprised between 10 and 100, preferably between 20 and 40;

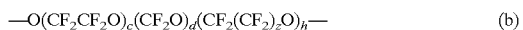 (b)

wherein c, d and h are integers such that the molecular weight is comprised in the range indicated; c/d is comprised between 0.1 and 10; h/(c+d) is comprised between 0 and 0.05, z has the value indicated above, h can also be equal to 0;

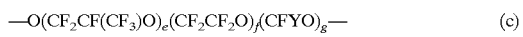 (c)

wherein Y is F or $CF_3$; e, f, g are integers such that the molecular weight is comprised in the range indicated; e/(f+g) is comprised between 0.1 and 10, f/g is comprised between 2 and 10;

 (d)

wherein: $R_{f'}$ is —$CF_3$, —$C_2F_5$, —$C_3F_7$; j,k,l are integers such that the molecular weight is comprised in the range indicated; k+l and j+k+l are at least equal to 2, k/(j+l) is comprised between 0.01 and 1000, 1/j is comprised between 0.01 and 100;

 (e)

wherein s is an integer such as to give the molecular weight indicated, z has the meaning already defined;

 (f)

wherein $R_4$ and $R_5$ are equal or different from each other and are selected from Cl or perfluoroalkyl, for instance from 1 to 4 C atoms, j' being an integer such that the molecular weight is that indicated;

 (g)

j" being an integer such as to give the molecular weight indicated.

These structures comprising the indicated repeating units and the methods for their preparation are described in the patents GB-1,104,482, U.S. Pat. Nos. 3,242,218, 3,665,041, 3,715,378, 3,665,041, EP-148,482, U.S. Pat. No. 4,523,039, 5,144,092.

The emulsions of perfluoropolyethers indicated above are obtained with a polymeric emulsifying system based on one or more modified, preferably acrylic, copolymers obtainable by copolymerization of a monoolefinic carboxylic acid, preferably acrylic acid, with an acrylic ester, generally an acrylic acrylate, having a long chain of aliphatic type, generally from 8 to 30 carbon atoms.

The modified polymer used as emulsifier generally contains an amount of carboxylic monomer in a range from 40 to 99% by weight, preferably from 50 to 98%, and still more preferably from 80 to 98%. Monomeric mixtures of one or more carboxylic monomers and one or more acrylic esters can be utilized. The polymer optionally can also be crosslinked by introducing in the monomeric mixture a crosslinking agent, generally in amounts comprised between 0.1 and 4% by weight, preferably 0.2 and 1%, based on the sum of the polymerized monomers. The crosslinking agent is generally a polymerizable monomer containing two or more double bonds. The carboxylic monomer generally contains from 3 to 6 carbon atoms. The preferred carboxylic monomers are of acrylic type and have the following formula:

$$CH_2=CR-COOH$$

wherein R is selected from H, halogen, OH, lactone, lactam, CN, alkylic, arylic, arylalkylic or alkylarylic, cycloaliphatic monovalent radicals from 1 to 20 C atoms, preferably from 1 to 6. The acrylic acid is preferred.

The preferred acrylic esters are alkyl(meth)acrylates having the formula:

$$CH_2=CR_1—COOR_2$$

wherein $R_1$ is H, $CH_3$, $C_2H_5$; $R_2$ is an alkylic group from 8 to 30 C atoms, or oxyalkylenes, or carbonyloxyalkylenes.

Oxyethylenes are preferred oxyalkylenes. Decyl (meth) acrylate, lauryl(meth)acrylate, stearyl(meth)acrylate, etc., can be mentioned.

As crosslinking agents, polyalkenylpolyethers can be used.

The modified polymers of the invention are obtained in an inert solvent wherein the polymer is not soluble in a meaningful amount, or the polymerization is carried out in aqueous medium. Among the solvents, benzene, xylene, hexane, ethyl acetate, etc., can be mentioned.

As polymerization initiators, persulphates of ammonium or of alkaline metals, benzoyl peroxide, cumene hydroperoxide, azoisobutyronitrile, redox catalysts can be mentioned.

The modified acrylic polymers are neutralized with bases to obtain the corresponding salts. Among the bases, the alkales and the substituted amines can be cited.

The emulsifiers known on the market Pemulen$^R$ TR by BF Goodrich, in particular Pemulen$^R$ TR-2 which is a copolymer based on acrylic acid and acrylic esters with an alkylic chain C10–30, are preferred.

The compositions of the invention, based on the combination of the components indicated above, show not only a very good stability both as regards the emulsion and the foam stability, but also an improved foam homogeneity.

When in contact with the skin, the foams of the present invention, although they are based on emulsions which have high stability, behave as quick breaking system and prompt release systems of the emollients and protective agents and at the same time with an homogeneous distribution of the latter in the skin application.

The component a) of the composition of the invention is an emulsion of the oil type in water which remains stable in the containers utilized for foams.

The polar and non polar oils which can be mentioned are the common natural and synthetic cosmetic emollients; in particular mineral oils, triglycerides, alcohols and/or fatty acids esters, silicones, can be mentioned.

Optional components which can be used are co-emulsifiers, such as fatty alcohols, ethoxylated greases; wetting and hydrating agents, such as glycerine, propylenic glycol, urea; chelants such as EDTA disodic salt.

The emulsion is generally prepared by dispersing the acrylic polymer, usually in the form of powder, in the oily phase which is added to the aqueous phase under stirring. Then the surfactant is added in the indicated amounts.

Preferably the emulsions of the present invention are obtained with the following procedure described in quite general terms:

part A (aqueous phase):
 demineralized water,
 optional wetting agents (glycerine, propylenic glycol),
 optional chelant,(EDTA),
part B (oil phase):
 emollients (mineral oil, ester, triglyceride),
 polymeric emulsifying agent (modified acrylic polymer),
part C:
 demineralized water,
 neutralizing agent (soda, triethanolamine, etc.),
part D:
 perfluoropolyether.

In a container having a sufficient volume for the whole emulsion, demineralized water is added, in which the microbic conservants and the other ingredients soluble in water are dissolved (wetting agents such as glycerine or propylenic glycol, chelants as EDTA, etc.) (part A). To the aqueous phase it is added, under stirring and at room temperaure, the oily phase (part B) in which the emulsifying agent is dispersed.

One proceeds to the almost neutralization up to a pH around 6 by addition of an alkaline compound dissolved in water (part C), always under stirring and at room temperature.

Perfluoropolyether (part D) is gradually added under strong stirring which is maintained for 15–20 minutes.

Then the foaming agent is added.

The emulsion thus obtained is placed under pressure in a 210 ml closed container by addition of 30 parts by volume of a liquefied gas to 120 parts by volume of the emulsion itself.

The obtained emulsion with the procedure previously described is white, fine and fluid.

The viscosity of the emulsions of the invention is generally comprised between 200 and 5000 cPs, preferably between 300 and 2000 cPs. The emulsion is considered stable if no segregation occurs after 60 days in stove at 40° C. or in centrifuge at 4000 rpm for 10 minutes.

The emollients are preferably a combination of polar and non polar emollients.

The emulsifying agent of the invention as said is obtained by neutralization with addition of neutralizing agents, preferably triethanolamine, so as to have a pH comprised between 5.5 and 6.5.

The foaming agent is a surfactant of ionic type, both of anionic, amphoteric and cationic type, preferably of anionic type.

The surfactants which can be mentioned are preferably those active with a pH between 4 and 8, and still more preferably between 5.5 and 6.5.

The surfactants which can be mentioned as an example: carboxylates, sarcosinates, sulphosuccinates, alkyl ethers sulphates; for the cationic ones, the amines oxides can be mentioned; for the amphoteric the betaines.

As already said, the concentration of the foaming agent is comprised between 0.1 and 5%, preferably between 0.3 and 1.5%; they are generally used in aqueous solutions (generally with a titre comprised between 20 and 50% by weight).

The liquefied gas acting as a propellant, is any propellant, preferably a liquefied hydrocarbon and specifically isobutane, or hydrofluorohydrocarbons such as 125, 134a, 227e, obviously mixtures of the mentioned propellants also belonging to different classes, can be utilized.

Some illustrative but non limitative Examples of the present invention are reported hereinafter.

EXAMPLE 1

An emulsion of the following composition (parts by weight) has been prepared, by adopting the previous procedure:

| | |
|---|---|
| mineral oil (emollient) | 10 |
| caprylic/capric tryglicerid (emollient) | 5 |
| cetearyl-isononaoate (emollient) | 5 |
| Pemulen ® TR-2 (emulsifier) | 0.19 |
| parabens (conservants) | as it suffices |
| water | up to 100 |
| triethanolamine | 0.16 |
| EDTA | 0.10 |

To this emulsion with a viscosity of 2900 cPs, measured with a Brookfield DV II, 10 rpm it is added as foaming agent 1 part by weight of Empicol$^R$ CED 5/5 (Albright & Wilson, Great Britain), chemical name laurylether (6) sodium carboxylate (name CTFA/INCI: "Sodium Laureth-6 Carboxylate"), the titre of this ionic surfactant is 23% by weight in water, obtaining a viscosity of 1700 cPs. The emulsion resulted stable (absence of segregation) after two months at 40° C., with the viscosity decreasing to 1590 cps.

The addition of isobutane as propellant, 30 ml per 120 ml of emulsion, allows to obtain a foam. The foam breaks very quickly in a time of 20–25 minutes, with formation of an homogeneous stain, as it was verified by the homogeneity test defined above.

EXAMPLE 2

One proceeds as in the Example 1, but in this case the foaming agent is used in concentration of 5 parts.

The emulsion results stable (absence of segregation) after two months at 40° C. according to the test defined above.

EXAMPLE 3

One proceeds as in Example 1, but in this case it is used as foaming agent 1 part by weight of Produkt$^R$ GM90-11, (Zschimmer & Schwarz, Germany), sodium laurylsarcosinate (name CTF-A/INCI: "Sodium Lauroyl Sarcosinate"), the titre of this ionic surfactant is 29% by weight in water. The viscosity decreases to 1900 cps.

The emulsion resulted stable (without segregation) after two months according to the test as defined; the viscosity decreases to 800 cPs.

The obtainable foam has the characteristics of the foam of Example 1 by the homogeneity test.

EXAMPLE 4

One proceeds as in Example 1, but in this case it is used as foaming agent 2 parts of Texapon$^R$ XP3 (Henkel, Germany), chemical name sodium laurylethersulfosuccinate (name CTFA/INCI: "Disodium Laureth Sulfosuccinate"), the titre of this ionic surfactant is 29% by weight in water.

The viscosity after two months decreases to 550 cPs without segregation (stability test).

The obtainable foam has the characteristics of the foam of Example 1 by the homogeneity test but the time required for its homogenization is 40–45 minutes.

EXAMPLE 5 (comparative)

One proceeds as in Example 1, but in this case it is used as foaming agent 1 part by weight of Plantacare$^R$ 818 (Henkel, Germany), chemical name: coco glucoside (name CTFA/INCI: "Coco Glucoside"), the titre of this non ionic surfactant: 29% by weight in water.

The emulsion resulted unstable (segregation) after one week at 40° C. by the stability test.

An emulsion of this type, therefore, is not suitable for preparing foams which are used also after a long shelf life. However the Applicant has prepared all the same a foam with this emulsion by operating as in Example 1.

At the homogeneity test the stain does not result homogeneous and therefore it is not suitable to prepare foams to be used as liquid glove for the protection from the irritating agent indicated in the description.

EXAMPLE 6 (comparative)

One proceeds as in Example 1, but in this case it is used as foaming agent 1 part by weight of Plantacare$^R$ 2000 (Henkel, Germany), chemical name: laurylglucoside (name CTFA/INCI: "Lauryl Glucoside"), the titre of this non ionic surfactant is 50% by weight in water.

The emulsion resulted unstable (segregation) after two days at 40° C. by the stability test.

The foam obtained has the same characteristics as that of Example 5.

EXAMPLE 7

An emulsion was prepared with the following composition (parts by weight):

| | |
|---|---|
| mineral oil (emollient) | 10 |
| caprylic/capric tryglicerid (emollient) | 5 |
| Pemulen ® TR-2 (emulsifier) | 0.3 |
| parabens (conservants) | as it suffices |
| EDTA (chelant) | 0.10 |
| water | up to 100 |
| triethanolamine (neutralizer) | 0.26 |
| perfluoropolyether (Fomblin ® HC/04, PM = 1500) | 0.5 |

The addition of 5 parts by weight of foaming agent Empicol$^R$ CED 5/5 (see Example 1) as foaming agent, leads to a stable emulsion after 2 months at 40° C. by the stability test.

EXAMPLE 8

An emulsion was prepared with the following composition (parts by weight):

| | |
|---|---|
| mineral oil (emollient) | 10 |
| octyl palmitate (emollient) | 10 |
| Pemulen ® TR-2 (emulsifier) | 0.25 |
| parabens (conservants) | as it suffices |
| water | up to 100 |
| triethanolamine (neutralizer) | 0.2 |
| perfluoropolyether (Fomblin ® HC/25, PM = 3200) | 5 |

To this emulsion (viscosity 320 cPs, measured with a Brookfield DV II, 10 rpm) it is added as foaming agent 1 part by weight of Bedadet$^R$ HR (Kao Corp., Japan), chemical name: cocoamidopropybetaine (name CTFA/INCI: "Coco Amido Propyl Betaine"), the titre of this non ionic surfactant is 30% by weight in water.

The viscosity does not meaningfully change and there is no segregation after centrifugation (at 4000 rpm for 10 minutes) by the stability test.

EXAMPLE 9 (comparative)

One operates as in Example 8, but by using as foaming agent 1 part by weight of Levenol$^R$ C-642 (Kao Corp., Japan), chemical name: PEG-30 glycerylcocoate (name CTFA/INCI: "PEG-30 Glyceryl Cocoate"), the titre of this non ionic surfactant is about 100% by weight.

By the stability test after centrifugation there is segregation.

EXAMPLE 10 (comparative)

One operates as in Example 8, but by using as foaming agent 1 part by weight of Plantacare$^R$ 1200 (Henkel, Germany), chemical name: laurylglucoside (name CTFA/INCI: "Lauryl Glucoside"), the titre of this non ionic surfactant is 50–60% by weight in water.

By the stability test after centrifugation there is segregation.

EXAMPLE 11 (comparative)

One operates as in example 8, but by using as foaming agent 1 part by weight of Plantacare$^R$ 2000 (Henkel, Germany), chemical name: decylglucoside (name CTFA/INCI: "Decyl Glucoside"), the titre of this non ionic surfactant is 50–60% by weight in water.

After centrifugation there is segregation by the stability test.

EXAMPLE 12 (comparative)

One operates as in Example 8, but by using as foaming agent 1 part by weight of Tween$^R$ 80 (ICI Surfactants, Belgium), chemical name: mono ester of oleic ethoxylate acid (name CTFA/INCI: "Polysorbate 80"), the titre of this non ionic surfactant is about 100% by weight.

After centrifugation there is segregation by the stability test.

EXAMPLE 13

One operates as in Example 8, but by using as foaming agent 1 part by weight of Texapon$^R$ N/40 (Henkel, Germany), chemical name: sodium laurylethersulphate (name CTFA/INCI: "Sodium Laureth Sulfate"), the titre of this anionic surfactant is 28% by weight in water.

After centrifugation there is no segregation by the stability test.

EXAMPLE 14

One operates as in Example 8, but by using as foaming agent 1 part by weight of Ammonyx$^R$ LO (Goldschmidt Italy, Italy), chemical name: lauryldimethyl amine oxide (name CTFA/INCI: "Lauramine Oxide"), the titre of this cationic surfactant in acid ambient is 30% by weight in water.

After centrifugation there is no segregation by the stability test.

EXAMPLE 15

One operates as in Example 8, but by using as foaming agent 1 part by weight of Ammonyx$^R$ CDO (Goldschmidt Italy, Italy), chemical name: alkylamido amine oxide (name CTFA/INCI: "Alkyl Amido Propylamine Oxide"), the titre of this cationic surfactant in acid ambient is 30% by weight in water.

After centrifugation there is no segregation by the stability test.

EXAMPLE 16

An emulsion of the following composition (parts by weight) was prepared:

| | |
|---|---|
| mineral oil (emollient) | 10 |
| caprylic/capric triglycerid (emollient) | 5 |
| benzoate of the C12–15 alcohol (emollient) | 5 |

-continued

| | |
|---|---|
| acrylic copolymer Pemulen ® TR-2 (emulsifier) | 0.18 |
| triethanolamine (neutralizer) | 0.12 |
| conservants | as it suffices |
| water | up to 100 |
| perfluoropolyether (Fomblin ® HC/R) | 4 |

To this emulsion, having a viscosity of 1900 cPs, 3 parts by weight of the foaming agent AmmonyxR CDO (see Example 15), were added.

By the stability test there is no destabilization of the emulsion (stable 2 months at 40° C.).

The emulsion was then put under pressure by addition of 30 parts (by volume) of isobutane to 120 parts by volume of emulsion.

A foam looking as that of Example 1 as to homogeneity but with homogenization times of 3–4 hours is obtained.

EXAMPLE 17 (comparative)

An amount, comprised between 0.5 and 1 g, of the commercial foam Proderma$^R$ by AB Pondus (Sweden) is applied on a A4 paper sheet, by delivery from the bomb.

When the foam is completely damped there is no formation of an homogeneous stain on the paper sheet, but there is formation of a non uniform residue which can be removed without leaving traces on the paper.

EXAMPLE 18 (comparative)

The same experimental procedure described in Example 17 is followed by applying a commercial foam Restiva Professional$^R$ by Restiva Italiana. The behaviour of the foam is similar to that noticed in Example 17.

EXAMPLE 19 (comparative)

The same experimental procedure described in Example 17 is followed by applying a commercial foam Marly Skin$^R$ distributed by Gebro Pharma in Germany and by Trimex Trading in Switzerland. The behaviour of the foam is similar to that noticed in Example 17.

EXAMPLE 20 (comparative)

The same experimental procedure described in Example 17 is followed by applying a commercial foam Linola Protect$^R$ of Dr August Wolff GmbH (Germany). The behaviour of the foam is similar to that noticed in Example 17.

EXAMPLE 21 (comparative)

The same experimental procedure described in Example 17 is followed by applying a commercial foam Dermary$^R$ distributed in Italy by Maryl Italia. The behaviour of the foam is similar to that noticed in Example 17.

I claim:

1. Foams based on the following components:
   a) a fluid emulsion comprising:
      a perfluoropolyether, as main protective agent,
      polar and non polar oils,
      an acrylic copolymer characterized by hydrophilic and hydrophobic groups, and activity of primary emulsifier after neutralization with alkales,
      an ionic surfactant (as foaming agent),
      water
   b) a propellant.

2. Foams according to claim 1 wherein the amount of the foaming agent is comprised between 0.1 and 5 parts, per 100 parts of emulsion.

3. Foams according to claim 1 wherein the emulsion for obtaining foams contains the components indicated in the following amounts (parts by weight):
a perfluoropolyether in amounts from 0.05 to 30 parts, (by weight), the average number molecular weight is comprised between 500 and 10000,
polar and non polar oils from 5 to 40 parts,
an acrylic copolymer characterized by hydrophillic and hydrophobic groups, and activity, after neutralization with bases, of primary emulsifier, whose concentration is comprised in the range 0.1–0.5 parts by weight,
an ionic surfactant (as foaming agent) the amount of which is comprised between 0.1 and 5 parts by weight,
water as complement to 100 parts by weight.

4. Foams according to claim 1 wherein the amount of propellant is between 20 and 40 parts by volume for 120 parts by volume of emulsion.

5. Foams according to claim 1, wherein the perfluoropolyethers (PFPE) comprise repeating units statistically distributed along the polymer chain selected from:
$(CF_2CF_2O)$, $(CFYO)$ wherein Y is equal to F or $CF_3$, $(C_3F_6O)$, $(CF_2(CF_2)_zO)$ wherein z is an integer equal to 2 or 3, $(CF_2CF(OR_f)O)$, $(CF(OR_f)O)$ wherein $R_f$ is equal to $-CF_3$, $-C_2F_5$, $-C_3F_7$; $CR_4R_5CF_2CF_2O$ wherein $R_4$ and $R_5$ are equal to or different from each other and selected from Cl or perfluoroalkyl, for instance from 1 to 4 C atoms; the perfluoropolyethers end groups are selected from $-CF_3$, $-C_2F_5$, $-C_3F_7$, $ClCF_2CF(CF_3)-$, $CF_3CFClCF_2-$, $ClCF_2CF_2-$, $ClCF_2-$.

6. Foams according to claim 5 wherein the (per)fluoropolyethers have the following repeating units:

$$-O(CF_2CF(CF_3)O)_a(CFYO)_b- \quad (a)$$

wherein Y is F or $CF_3$; a and b are integers such that the molecular weight is in the range indicated; a/b is comprised between 10 and 100;

$$-O(CF_2CF_2O)_c(CF_2O)_d(CF_2(CF_2)_zO)_h- \quad (b)$$

wherein c, d and h are integers such that the molecular weight is comprised in the range indicated; c/d is comprised between 0.1 and 10; h/(c+d) is comprised between 0 and 0.05, z has the value indicated above, h can also be equal to 0;

$$-O(CF_2CF(CF_3)O)_e(CF_2CF_2O)_f(CFYO)_g- \quad (c)$$

wherein Y is F or $CF_3$; e, f, g are integers such that the molecular weight is comprised in the range indicated; e/(f+g) is comprised between 0.1 and 10, f/g is comprised between 2 and 10;

$$-O(CF_2O)_j(CF_2CF(OR_f)O)_k(CF(OR_f)O)_l- \quad (d)$$

wherein: $R_f''$ is $-CF_3$, $-C_2F_5$, $-C_3F_7$; J, K, L are integers such that the molecular weight is comprised in the range indicated; K+l and J+k+l are at least equal to 2, k/(j+l) is comprised between 0.01 and 1000, l/j is comprised between 0.01 and 100;

$$-O(CF_2(CF_2)_zO)_s- \quad (e)$$

wherein s is a integer such that the molecular weight is comprised in the range indicated, z has the meaning already defined;

$$O(CR_4R_5CF_2CF_2O)_{j'}- \quad (f)$$

wherein $R_4$ and $R_5$ are equal or different from each other and are selected from Cl or perfluoroalkyl, j' being an integer such that the molecular weight is comprised in the range indicted;

$$-O(CF(CF_3)CF_2O)_{j''}- \quad (g)$$

j" being an integer such that the molecular weight is comprised in the range indicated.

7. Foams according to claim 1, wherein the emulsifying agent is based on one or more modified acrylic copolymers, obtained by copolymerization of a monoolefinic carboxylic acid with an acrylic ester.

8. Foams according to claim 7 wherein the emulsifying agent contains an amount of carboxylic monomer in a range from 40 to 99% by weight.

9. Foams according to claim 7 wherein the emulsifying agent obtained by polymerization of monomeric mixtures of one or more carboxylic monomers and one or more acrylic esters, is crosslinked by introducing in the monomeric mixture a crosslinking agent, in amounts comprised from 0.1 to 4% by weight.

10. Foams according to claim 7 wherein the crosslinking agent is a polymerizable monomer containing two or more double bonds.

11. Foams according to claim 7 wherein in the emulsifying agent the carboxylic monomer has the formula:

$$CH_2=CR-COOH$$

wherein R is selected from H, halogen, OH, lactone, lactam, CN, alkylic, arylic, arylalkylic or alkylarylic, cycloaliphatic monovalent radicals from 1 to 20 C atoms; the acrylic esters are alkyl(meth)arcylates having the formula:

$$CH_2=CR_1-COOR_2$$

wherein $R_1$ is H, $CH_3$, $C_2H_5$; $R_2$ is an alkylic group from 8 to 30 C atoms, or oxyalkylenes, or carbonyloxyalylenes.

12. Foams according to claim 1 wherein the polar and non polar oils are the common natural and synthetic cosmetic emollients, selected from the group consisting of mineral oils, triglycerides, alcohols and/or fatty acids esters, silicones.

13. Foams according to claim 1, further comprising optional components as co-emulsifiers, wetting and hydrating agents, and chelants.

14. Foams according to claim 1 wherein the emulsifying agent obtained by neutralization by addition of neutralizing agents, has a pH comprised between 5.5 and 6.5.

15. Foams according to claims 1–14 wherein the foaming agent is a surfactant of ionic type selected from the group consisting of anionic, amphoteric or cationic surfactant.

16. Foams according to claim 15 wherein the foaming agent is active with a pH comprised between 4 and 8 selected from the group consisting of carboxylates, sarcostinates, sulfosuccinates, alkyl ether sulphates amines oxides, and betaines.

17. Use of foams according to claim 1, wherein they are used as protective agents towards irritating agents.

18. Fluid emulsions according to claim 1.

19. Process for preparing foams according to claims 1–16, wherein the emulsion is obtained by preparing:
art A (aqueous phase):
  demineralized water,
  optional wetting agents (glycerine, propylenic glycol),
  optional chelant (EDTA),
part B (oil phase):
  emollients (mineral oil, ester, triglyceride),
  polymeric emulsifying agent (modified acrylic polymer),
part C:
  demineralized water,
  neutralizing agent (soda, triethanolamine),
part D:
  perfluoropolyether;
then in demineralized water microbic conservants and the other ingredients soluble in water are dissolved (wetting agents, chelants) (part A); further to the aqueous phase, under stirring and at room temperaure, the oily phase (part B), in which the emulsifying agent is dispersed, is added; then follows the neutralization up to a pH around 6 by addition of an alkaline compound dissolved in water (part C), under stirring and at room temperature; then perfluoropolyether (part D) is gradually added under strong stirring which is maintained for 15–20 minutes; then the foaming agent is added; then the emulsion is placed under pressure by addition of 30 parts by volume of a liquefied gas to 120 parts by volume of the emulsion.

20. Foams according to claim 2 wherein the amount of the foaming agent is comprised between 0.3 and 3 parts per 100 parts of emulsion.

21. Foams according to claim 20 wherein the amount of the foaming agent is comprised between 0.5 and 1.5 parts per 100 parts of emulsion.

22. Foams according to claim 3 wherein the emulsion contains a perfluoropolyether in amounts from 0.5 parts up to 5 parts (by weight) having the average number molecular weight comprised between 3000 and 7000 and polar and non polar oils from 10 to 20 parts (by weight).

23. Foams according to claim 6 wherein in the repeating units (a) of the (per)fluoropolyethers, the a/b is between 20 and 40.

24. Foams according to claim 8 wherein the emulsifying agent contains an amount of carboxylic monomer in a range from 50 to 98% by weight.

25. Foams according to claim 24 wherein the emulsifying agent contains an amount of carboxylic monomer in a range from 80 to 98% by weight.

26. Foams according to claim 9 wherein the crosslinking agent is in amount between 0.2 to 1% based on the sum of the polymerized monomers.

27. Foams according to claim 11 wherein the radical R of the general formula is cycloalyphatic monovalent radicals from 1 to 6 carbon atoms.

28. Foams according to claim 11 wherein the carboxylic monomer is the acrylic acid.

29. Foams according to claim 12 wherein the polar and non-polar oils are mineral oils.

30. Foams according to claim 13 wherein said optional components are alcohols, glycerine, EDTA disodic salt.

31. Foams according to claim 14 wherein the neutralizing agent is triethanolamine.

32. Foams according to claim 15 wherein the foaming agent is an anionic surfactant.

33. Foams according to claim 16 wherein the foaming agent is active with a pH comprised between 5.5 and 6.5.

\* \* \* \* \*